United States Patent [19] [11] 4,166,069
Schimpf [45] Aug. 28, 1979

[54] PROCESS FOR THE PREPARATION OF 2-METHOXY-5-METHYLANILINE-4-SULPHONIC ACID

[75] Inventor: Rolf Schimpf, Leverkusen, Fed. Rep. of Germany

[73] Assignee: Bayer Aktiengesellschaft, Leverkusen, Fed. Rep. of Germany

[21] Appl. No.: 882,293

[22] Filed: Feb. 27, 1978

[30] Foreign Application Priority Data

Mar. 30, 1977 [DE] Fed. Rep. of Germany ....... 2714031

[51] Int. Cl.² ............................................ C07C 143/64
[52] U.S. Cl. .................................................... 260/509
[58] Field of Search ................................ 260/508, 509

[56] References Cited

U.S. PATENT DOCUMENTS

| | | | |
|---|---|---|---|
| 2,821,525 | 1/1958 | Waitkins et al. | 260/508 |
| 3,519,617 | 7/1970 | Rast et al. | 260/200 |

*Primary Examiner*—Nicky Chan
*Attorney, Agent, or Firm*—Sprung, Felfe, Horn, Lynch & Kramer

[57] ABSTRACT

A process for the preparation of 2-methoxy-5-methylaniline-4-sulphonic acid by contacting optionally acylated 2-methoxy-5-methylaniline with sulfuric acid or a mixture of sulfuric acid and oleum at an elevated temperature.

9 Claims, No Drawings

PROCESS FOR THE PREPARATION OF 2-METHOXY-5-METHYLANILINE-4-SULPHONIC ACID

The invention relates to a process for the preparation of 2-methoxy-5-methylaniline-4-sulphonic acid by reacting optionally acylated 2-methoxy-5-methylaniline with sulphuric acid or mixtures of sulphuric acid and oleum.

It is known that anisidinesulphonic acid can be prepared by sulphonating anisidines, the anisidines being sulphonated in the o-position and p-position relative to the methoxyl group (compare, for example, Houben-Weyl, Methoden der organischen Chemie (Methods of Organic Chemistry), 4th edition, Georg Thieme-Verlag, Stuttgart, 1955, Volume IX, page 473). Thus 1-methoxy-2-aminobenzene-4-sulphonic acid is formed from o-anisidine (BIOS Final Report 1153, 179 (1946)). If the p-position is occupied, the sulpho group is introduced in the 6-position relative to the hydroxyl or methoxy group. For example, 4-chloro-2-amino-phenol-6-sulphonic acid is obtained from 4-chloro-2-amino-phenol (Houben-Weyl, see above, page 472).

A process has been found for the preparation of 2-methoxy-5-methylaniline-4-sulphonic acid, which is characterised in that optionally acylated 2-methoxy-5-methylaniline is reacted with sulphuric acid or a mixture of sulphuric acid and oleum at elevated temperature.

Examples of acyl groups which may be mentioned are: formyl-, acetyl-, propionyl- and benzoyl-.

The process according to the invention can be represented by the following equation, using 2-methoxy-5-methylaniline as an example.

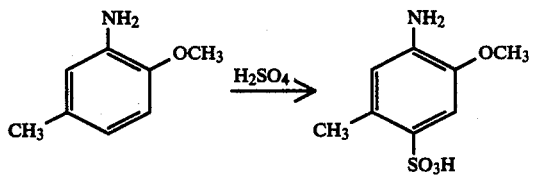

The reaction of the optionally acylated 2-methoxy-5-methylaniline can be carried out with 3 to 8 mols of sulphuric acid, preferably 4 to 5 mols of sulphuric acid, relative to 1 mol of starting material, at temperatures in the range from about 90° to 130° C., preferably at 100° to 110° C. In this procedure, the sulphuric acid can be employed in a concentration in the range from about 96 to 100% by weight, preferably in a concentration of 100% by weight.

In general, the procedure is to initially introduce the sulphuric acid and to meter in the starting material, whilst stirring and cooling. In order to bring the reaction to completion, it is advantageous to heat the reaction mixture and, after the reaction has ended, to add the mixture to water, which is optionally prewarmed slightly, whereupon the sulphonic acid precipitates. The precipitated reaction product can the be filtered off on a suction filter.

According to another variant, the reaction of the optionally acylated 2-methoxy-5-methylaniline can be carried out in a mixture of concentrated sulphuric acid (100% strength by weight) and oleum, which contains 20 to 65% by weight, preferably 20% by weight, of $SO_3$. In this procedure, the weight ratio of sulphuric acid to oleum is about 0.3:1 to about 3:1, in the case of 20% strength oleum, preferably 0.40:1 to 0.65:1. The molar ratio of sulphuric acid to starting material should be about 1.3:1 to 8:1, preferably 1.9:1 to 3:1; and the molar ratio of $SO_3$ to starting material should be about 1:1 to about 1.3:1, preferably 1.07:1 to 1.1:1.

The reaction can be carried out by initially introducing sulphuric acid and adding the optionally acylated 2-methoxy-5-methylaniline, whilst stirring and cooling. After adding the oleum, the reaction solution is warmed to about 20° to 100° C., preferably 60° to 70° C., until the reaction has ended. The reaction solution is stirred into water, whereupon the sulphonic acid precipitates. The suspension, which becomes warm during this procedure, is cooled to about 20° C. and the reaction product is then filtered off.

It was surprising that when 2-methoxy-5-methylaniline, that is to say an o-anisidine derivative, is sulphonated 2-methoxy-5-methylaniline-4-sulphonic acid is obtained, in good yields, and not 2-methoxy-5-methylaniline-3-sulphonic acid, as would be expected from the literature.

2-Methoxy-5-methylaniline-4-sulphonic acid is used, for example, for the preparation of dyestuffs for foodstuffs (U.S. Pat. No. 3,519,617).

The process according to the invention may be illustrated with the aid of the following examples, but without limiting it to these examples.

EXAMPLE 1

100 ml of sulphuric acid (100% strength) are initially introduced and 137 g (1 mol) of 2-methoxy-5-methylaniline are introduced in the course of 30 to 90 minutes at 20° to 30° C., whilst stirring and cooling with an ice-bath. 440 g of oleum (20% strength) are then added dropwise to the light brown, thick suspension in the course of one hour. The temperature is thereby allowed to rise to 60° C., whereupon the suspension becomes thinner. When all the oleum has been added dropwise, an almost clear, dark red solution is formed. The reaction mixture is warmed to 65° C.; all the solid thereby dissolves. The solution is stirred at 60° to 65° C. for a further 2 hours. After the reaction has ended, the sulphonation mixture is added dropwise into 1,080 ml of water, having a temperature of 50° C., in the course of one hour, whereupon the sulphonic acid precipitates. The temperature thereby rises to 80° C. Thereafter, the suspension is cooled to 20° C. by means of an ice-bath and the product is filtered off. The filter cake is then washed three times with 250 ml of water. A grey-white powder is obtained.

Yield: 227 g with a content of 86%, that is to say 195 g, of pure product=90% of theory.

EXAMPLE 2

260 ml of sulphuric acid (100% strength) are initially introduced and 137 g (1 mol) of 2-methoxy-5-methylaniline are introduced in the course of 30 minutes, whilst stirring and cooling with an ice-bath. The reaction mixture is subsequently heated to 100° C. for 13 hours and is then discharged onto 716 g of ice. The precipitate is filtered off and washed with 700 ml of water.

Yield: 344 g of product with a content of 52.2%, that is to say 179.6 g, of pure product=83% of theory.

EXAMPLE 3

100 ml of sulphuric acid (100% strength) are initially introduced and 179 g (1 mol) of 2-methoxy-5-methylacetanilide are introduced in the course of 45 minutes at 20° to 40° C., whilst stirring and cooling. 440 g of oleum (20% strength) are then added dropwise at 30° to 60° C. in the course of 40 minutes. A dark solution is thereby formed. The solution is subsequently stirred at 60° C. for a further hour and the reaction mixture is then discharged onto 1,100 ml of water. Thereafter, the reaction mixture is heated to 95° to 100° C. for 2 hours. A grey precipitate thereby separates out. After cooling to 20° C., the precipitate is filtered off and washed three times with 250 ml of water each time.

This gives 303 g of 64.4% strength product, that is to say 198.2 g of pure product.

Yield=91% of theory.

EXAMPLE 4

200 ml of sulphuric acid (100% strength) are initially introduced and 137 g (1 mol) of 2-methoxy-5-methylaniline are introduced in the course of 1½ hours, whilst stirring, the temperature being allowed to rise to 50° C. 136 g of oleum (65% strength) are then added dropwise in the course of 30 minutes and the temperature is thereby allowed to rise to 80° C. The reaction mixture is kept at 80° C. for a further 2 hours and is then discharged onto 630 g of water having a temperature of 50° C. A grey precipitate thereby separates out and the temperature rises to 80° C. The mixture is cooled to 20° C. and the product is filtered off and washed three times with 250 ml of water each time.

Yield: 267 g of 67% pure product, that is to say 178.9 g of pure product=82% of theory.

What is claimed is:

1. Process for preparing 2-methoxy-5-methylaniline-4-sulphonic acid which comprises contacting 2-methoxy-5-methylaniline or an acylated derivative thereof with sulfuric acid or a mixture of sulfuric acid and oleum at an elevated temperature.

2. Process according to claim 1 wherein the reaction is carried out with 3 to 8 mols of sulfuric acid per mol of 2-methoxy-5-methylaniline or an acylated derivative thereof.

3. Process according to claim 1 wherein the sulfuric acid has a strength of 96 to 100% by weight.

4. Process according to claim 1 wherein the reaction is carried out at a temperature of from 90° to 130° C.

5. Process according to claim 1 wherein the reaction is carried out in a mixture of concentrated sulfuric acid and oleum which contains 20 to 65% by weight $SO_3$, the weight ratio of sulfuric acid to oleum being 0.3:1 to 3:1, the molar ratio of sulfuric acid to 2-methoxy-5-methylaniline or an acylated derivative thereof being 1.3:1 to 8:1 and the molar ratio of $SO_3$ to 2-methoxy-5-methylaniline or an acylated derivative thereof being 1:1 to 1.3:1.

6. A process according to claim 1 wherein the reaction is carried out at a temperature in the range of from 20° to 100° C.

7. Process according to claim 6 wherein the reaction is carried out at a temperature in the range of from 60° to 70° C.

8. A process according to claim 1 wherein said 2-methoxy-5-methylaniline is an acylated 2-methoxy-5-methylaniline.

9. A process according to claim 8 wherein the acyl group of the acylated 2-methoxy-5-methylaniline is formyl, acetyl, propionyl or benzoyl.

* * * * *